(12) United States Patent
Takahashi et al.

(10) Patent No.: US 6,348,622 B1
(45) Date of Patent: *Feb. 19, 2002

(54) VITAMIN A RELATED COMPOUNDS AND PROCESS FOR PRODUCING THE SAME

(75) Inventors: Toshiya Takahashi, Ibaraki; Shinzo Seko, Toyonaka; Takashi Miki, Ibaraki, all of (JP)

(73) Assignee: Sumitomo Chemical Company, Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/500,998

(22) Filed: Feb. 9, 2000

Related U.S. Application Data

(63) Continuation-in-part of application No. 09/138,894, filed on Aug. 24, 1998, now abandoned.

(30) Foreign Application Priority Data

| Aug. 25, 1997 | (JP) | ............................................. | 9-228195 |
| Oct. 24, 1997 | (JP) | ............................................. | 9-292314 |
| Dec. 11, 1997 | (JP) | ............................................. | 9-341270 |
| Dec. 11, 1997 | (JP) | ............................................. | 9-341271 |
| Jan. 27, 1998 | (JP) | ........................................... | 10-013887 |
| Feb. 4, 1998 | (JP) | ........................................... | 10-023416 |

(51) Int. Cl.$^7$ ........................ C07C 67/02; C07C 69/63; C07C 35/18; C07C 315/00; C07C 69/00
(52) U.S. Cl. ...................... 560/260; 560/231; 560/232; 560/129; 560/226; 560/227; 560/228; 560/249; 560/254; 560/261; 560/262; 560/265; 560/266; 568/824; 568/825; 568/826; 568/827; 568/34; 568/31; 568/28; 568/27
(58) Field of Search ................................ 560/260, 231, 560/232, 129, 226, 227, 228, 249, 254, 261, 262, 265, 266; 568/824, 825, 826, 827, 34, 31, 28, 27

(56) References Cited

FOREIGN PATENT DOCUMENTS

EP 0187259 7/1986

OTHER PUBLICATIONS

D. Strack et al: Z. Naturforsch., C: Biosci., vol. 35c, No. 9–10, 1980, pp. 675–681, XP002133293.

(List continued on next page.)

*Primary Examiner*—Johann Richter
*Assistant Examiner*—Elvis O. Prize
(74) *Attorney, Agent, or Firm*—Birch, Stewart, Kolasch & Birch, LLP

(57) ABSTRACT

There is provided a compound of the formula[I]:

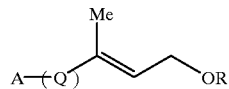

wherein R represents a hydrogen atom or a protective group for a hydroxyl group; and A represents a hydrogen atom, a halogen atom or a group of the formula A1:

A1

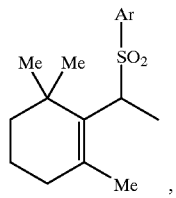

Q represents Q3:

Q3

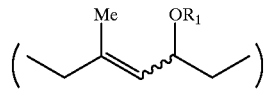

when A represents a halogen atom or a protective group for a hydroyl group, A represents Q4:

Q4

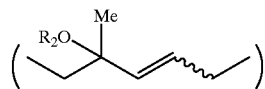

wherein $R_1$ and $R_2$ represent a hydrogen atom or a protective group for a hydroxyl group; and when A represents a hydrogen atom, Q is Q2:

Q2

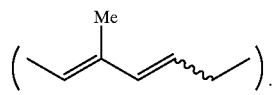

33 Claims, No Drawings

VITAMIN A RELATED COMPOUNDS AND PROCESS FOR PRODUCING THE SAME

This application is a continuation-in-part of application Ser. No. 09/138,894 filed on Aug. 24, 1998, now ABN entire contents of which are hereby incorporated by reference.

FIELD OF THE INVENTION

The present invention provides novel halohydrin compounds, sulfone compounds and triene compounds which are useful intermediates for producing Vitamin A and processes for producing the intermediate compounds and Vitamin A.

SUMMARY OF THE INVENTION

The present invention provides:

1. A compound of the formula[I]:

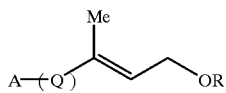

wherein R represents a hydrogen atom or a protective group for a hydroxyl group; and A represents a hydrogen atom, a halogen atom or a group of the formula A1:

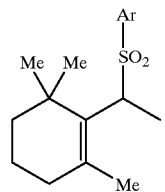

wherein Ar represents an aryl group which may be substituted; and when A represents A1, Q represents Q3:

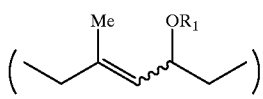

wherein $R_1$ represents a hydrogen atom or a protective group for a hydroxyl group;

when A represents a halogen atom, Q represents Q3 as defined above or Q4:

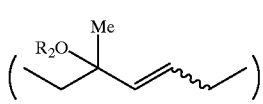

wherein $R_2$ represents a hydrogen atom or a protective group for a hydroxyl group;

when A represents a hydrogen atom, Q is Q2:

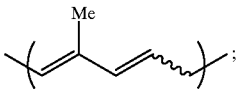

2. A process for producing retinol of the formula [X]

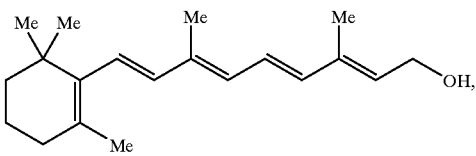

which comprises the steps of:

(a) subjecting a compound of the formula [III]:

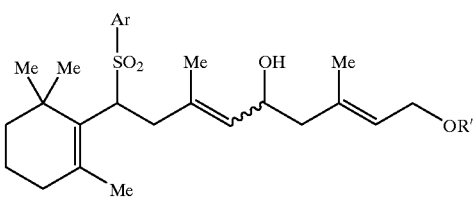

wherein R' represents a protective group for a hydroxyl group, to a reaction in the presence of a titanium tetrachloride, and (b) reacting the resulting compound in step (a) with a base(hereinafter referred to as "Process A");

3. A process for producing a compound of the formula [III]:

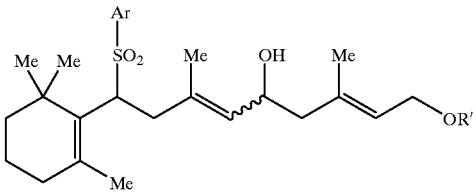

wherein Ar is an aryl group which may be substituted and R' is a protective group for a hydroxyl group, which comprises reacting a compound of the formula [IV]:

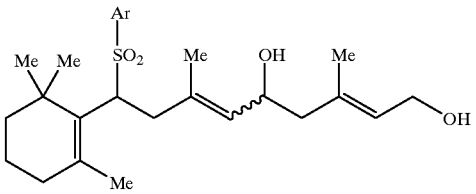

wherein Ar is the same as defined above, with a protective agent in the presence of a base and a phase transfer catalyst (hereinafter referred to as "Process B");

4. A process for producing a compound of the formula [V]:

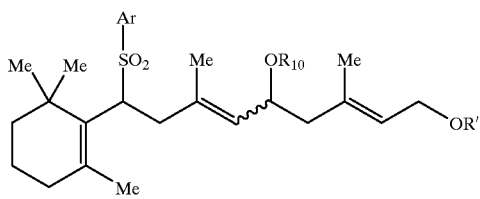

wherein Ar represents an aryl group which may be substituted, $R_{10}$ and R' are the same or different and represent a protective group for a hydroxyl group, which comprises reacting a sulfone compound of the formula [VI]:

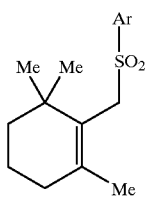

wherein Ar is the same as defined above, with a halohydrin compound of the formula [VII]:

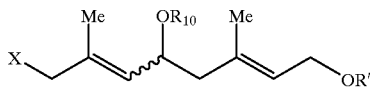

wherein $R_{10}$ and R' are as defined above, and X represents a halogen atom, in the presence of a base (hereinafter referred to as "Process C");

5. A process for producing a halohydrin compound of the formula [VII']:

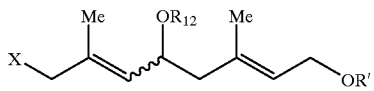

wherein $R_{12}$ represents an acyl group and R' represent a protective group for a hydroxyl group, and X represents a halogen atom, which comprises reacting at least one halohydrin compound selected from the group consisting of a compound of the formula [VII'a]:

and a compound of the formula [VII'b]:

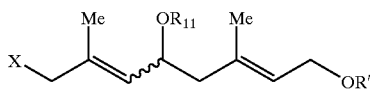

wherein $R_{11}$ represents an acyl group or a hydrogen atom and R' represents a protective group for a hydroxyl group, with a carboxylic acid of the formula:

$R_{12}OH$ wherein $R_{12}$ is the same as defined above, in the presence of a strong acidic catalyst (hereinafter referred to as "Process D");

6. A process for producing at least one halohydrin compound selected from the group consisting of the formula [VII'a]:

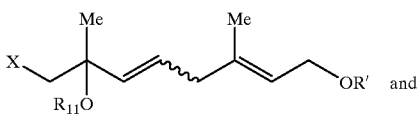 and a compound of the formula [VII'b]:

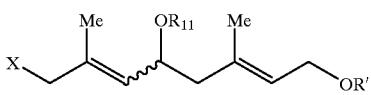

wherein $R_{11}$ represents an acyl group or a hydrogen atom and R' represents a protective group for a hydroxyl group, which comprises reacting a triene compound of the formula [VIII]:

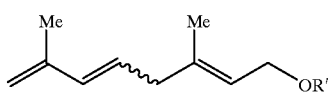

wherein R' is the same as defined above, with a halogenating agent and a compound of the formula:

$R_{11}OH$ wherein $R_{11}$ is is the same as defined above (hereinafter referred to as "Process E"); and 7. A process for producing the triene compound of the formula [VIII] as defined above, which comprises reacting a compound of the formula [IX]:

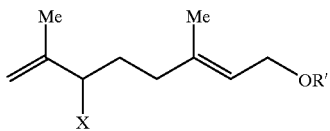

wherein X is a halogen atom and R' is a protective group for a hydroxyl group, with a base in the presence of a palladium catalyst, a phosphine ligand and a phase transfer catalyst (hereinafter referred to as "Process F").

DESCRIPTION OF THE PREFERRED EMBODIMENT

First a description will be made to the compound of the formula I.

The compound of the formula I above includes:

Compound [V]:

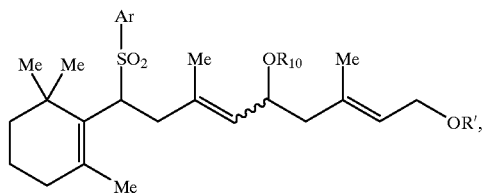

Compound [VII]:

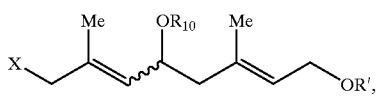

Compound [VII'a]:

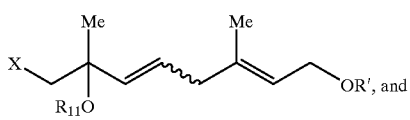

Compound [VIII]:

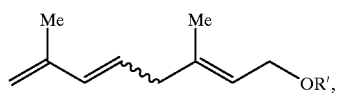

wherein R', $R_{10}$, $R_{11}$, X and Ar are the same as defined above.

In the present specification, a chemical bond indicated by "〰" means that the compound having the bond includes E isomer or Z isomer or both isomers with respect to a double bond connected to the said bond, and Compound [I] above has an optically active isomer and racemate thereof resulting from an asymmetric carbon atom present in the compound, which can be used in the following processes.

Examples of Ar group which may be substituted in the above formulas include a phenyl and naphthyl group which may be substituted.

Examples of the substituent include at least one substituent selected from a ($C_{1-C5}$)alkyl group (e.g., methyl, ethyl, n-propyl, i-propyl, n-butyl, t-butyl, s-butyl, n-pentyl), a ($C_1$–$C_5$)alkoxy group (e.g., methoxy, ethoxy, n-propoxy, i-propoxy, n-butoxy, t-butoxy, s-butoxy, n-pentoxy), a halogen atom(e.g., a fluorine, chlorine, bromine, or iodine atom), and a nitro group and the like.

Specific examples of Ar group which may be substituted include phenyl, naphthyl, o-tolyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl, p-nitrophenyl and the like.

Examples of the protective group for a hydroxyl group for R, R', $R_1$, $R_2$ and $R_{10}$ include:

an acyl group (an aliphatic or aromatic acyl group which may be substituted) such as acetyl, pivaloyl, benzoyl and p-nitrobenzoyl;

a silyl group such as trimethylsilyl, t-butyldimethylsilyl and t-butyldiphenylsilyl;

an alkoxymethyl group such as tetrahydrofuranyl, tetrahydropyranyl, methoxymethyl, methoxyethoxymethyl and 1-ethoxyethyl;

a benzyl group which may be substituted such as a benzyl group, a p-methoxybenzyl group and a trityl group;

a (C1–C6)lower alkyl group such as a t-butyl group, a methyl group;

a 2,2,2-trichloroethoxycarbonyl group;

an allyloxycarbonyl group and the like.

The acyl group described above may also includes those groups as defined for $R_{11}$ and $R_{12}$ below. The silyl group, alkoxymethyl group and a benzyl group described above may also include those defined for $R_{12}$ below.

Next description will be made to each Process A to F for producing Compound [I] and Vitamin A.

Process A

Retinol of the formula [X] can be industrially advantageously produced by a process which comprises the steps of:

(a) reacting a compound of the formula [III] as defined above to a reaction in the presence of titanium tetrachloride, and (b) reacting the resulting compound in step (a) with abase.

In step (a) an amount of titanium tetrachloride to be used is preferably 0.3–1.5 mol per mol of Compound [III].

In the above reaction, an organic solvent is usually used. Examples of the solvent include an ether solvent such as diethyl ether, tetrahydrofuran, dimethoxyethane and anisole; a hydrocarbon solvent such as n-hexane, cyclohexane, n-pentane, toluene and xylene; a halogenated solvent such as chloroform, dichloromethane, 1,2-dichloroethane, monochlorobenzene and o-dichlorobenzene; and an aprotic polar solvent such as N,N-dimethyl formamide, dimethyl sulfoxide, N,N-dimethyl acetamide, hexamethylphosphoric triamide.

A reaction temperature usually ranges from –78° C. to a boiling point of the solvent used, and preferably ranges from –10° C. to 50° C.

Next a description will be made to step (b).

Examples of the base used in this step include alkali metal hydroxide, alkaline earth metal hydroxide, alkali metal hydride, alkaline earth metal hydride, alkali metal alkoxide and alkaline earth metal alkoxide, and specific examples thereof include sodium hydroxide, potassium hydroxide, sodium hydride, potassium hydride, sodium methoxide, potassium methoxide, potassium t-butoxide, sodium t-butoxide and the like.

An amount of the base is usually about 2–20 mol per mol of the resulting compound in step (a).

In the above reaction, an organic solvent is usually used.

Examples of the solvent include a hydrocarbon solvent such as n-hexane, cyclohexane, n-pentane, toluene and xylene; an ether solvent such as diethyl ether, tetrahydrofuran, dimethoxyethane and anisole; and an aprotic polar solvent such as N,N-dimethyl formamide, dimethyl sulfoxide, N,N-dimethyl acetamide or hexamethylphosphoric triamide.

A reaction temperature is usually in the range from 0° C. to a boiling point of the solvent used, preferably in the range from about –10° C. to 50° C. After the reaction, Compound of the formula [X] can be obtained by conducting a conventional post-treatment, and may be purified by silica gel chromatography or the like, if necessary.

After completion of the reaction, protective groups of the compound obtained by the aforementioned reaction may be removed, if necessary, to give an alcohol compound by a conventional deprotection reaction as described in Protective Groups in Organic Synthesis, Greene and Wuts, 2nd Edition, (1992), John Wiley & Sons, Inc., the complete disclosure of which is incorporated hereinafter by reference.

For example, when the protective group is an acyl group, the deprotection can be usually conducted by reacting the compound with a base.

Alkoxide of alkali metal or alkaline earth metal or the like can be used as abase. An amount of the base used is usually 1 equivalent or more to Compound of the formula [III].

N,N-dimethyl formamide, N,N-dimethyl acetamide, dimethyl sulfoxide, tetrahydrofuran, alcohol, a mixed solvent of alcohol and water, a mixed solvent of tetrahydrofuran, water and the like can be used as a reaction solvent.

The reaction is usually carried out at from 0° C. to a boiling point of the reaction solvent used.

When the protective group is a silyl group or the like, the deprotection can be conducted by reacting the compound with tetra-n-butylammonium fluoride.

When the protective group is 2,2,2-trichloroethoxycarbonyl, a reductive deprotection can be performed using zinc dust and acetic acid.

Process B

Compound of the formula [III] can be produced by protecting a primary alcohol of Compound [IV].

The introduction of the protective group to the primary alcohol group of Compound of the formula [IV] is usually conducted by allowing Compound of the formula [IV] to react with a protective agent in the presence of a base and a phase-transfer catalyst.

The protective agent means a group consisting of a protective group and a leaving group (e.g., an active halogen atom or an acyloxy group) and includes an acyl halide, a benzyl halide which may be substituted, an alkoxymethyl halide, a silyl halide and an acid anhydride.

For example, the protective agent includes a compound of a formula: R'Y, wherein R' is an acyl group, an alkoxymethyl group, a benzyl group which may be substituted or a silyl group which may be substituted with three groups selected from a phenyl and a (C1–C6)lower alkyl group, and Y is a halogen atom such as chlorine, bromine and iodine and when R' is an acyl group, Y may be an acyloxy group corresponding to the acyl group as defined for R' above.

The acyl group may be an aliphatic or aromatic acyl group which may be substituted, and may also include those groups as defined for $R_{12}$ below. Specific examples thereof include acetyl, pivaloyl, benzoyl, p-nitrobenzoyl, 2,2,2-trichloroethoxycarbonyl and allyloxycarbonyl.

Examples of the alkoxymethyl group include methoxymethyl and methoxyethoxymethyl.

Examples of the benzyl group which may be substituted include a benzyl group, p-methoxybenzyl group and a trityl group.

Examples of the silyl group include trimethylsilyl, t-butyldimethylsilyl, t-butyldiphenylsilyl and the like.

Among these, an acyl halide is preferably used. Acetyl chloride is particularly preferably employed.

Examples of the acid anhydride include acetic anhydride, propionic anhydride, butyric anhydride and the like, and acetic anhydride is preferably used.

The protective agent is usually used in an amount of about 0.1 to 1.1 mol, per mol of Compound of the formula [IV].

In this reaction, an organic base or an inorganic base is used as the base, and the inorganic base is preferably used.

Examples of the organic base include pyridine, 4-dimethylaminopyridine, 3-ethyl-4-methylpyridine, 5-ethyl-2-methylpyridine, imidazole, 2-methylimidazole, 3-methylimidazole, 2-ethyl-4-methylimidazole, DBU, trimethylamine, triethylamine, dimethylethylamine, methyldiethylamine, diisopropylethylamine, t-butyldimethylamine and the like.

Examples of the inorganic base include hydroxide of an alkali metal or an alkaline earth metal, a carbonate of an alkali metal or an alkaline earth metal, a hydrogencarbonate of an alkali metal or an alkaline earth metal and the like.

Specific examples of the inorganic base includes, for example, sodium hydroxide, potassium hydroxide, sodium carbonate, potassium carbonate, sodium hydrogencarbonate, potassium hydrogencarbonate, calcium carbonate, calcium hydroxide and the like.

A solid inorganic base is preferably used in a fine powder form.

An amount of the base used usually ranges about 1–5 moles per mol of Compound of the formula [IV].

A phase-transfer catalyst is also usually employed.

Examples of the phase-transfer catalyst used in the reaction include a quaternary ammonium salt, a quaternary phosphonium salt, a sulfonium salt and the like, and the quaternary ammonium salt is preferably used.

As the quaternary ammonium salt, one comprising groups optionaly selected from alkyl and aryl having 1–24 carbon atoms is used.

Examples of the quaternary ammonium salt include, for example, tetramethylammonium chloride, tetraethylammonium chloride, tetrapropylammonium chloride, tetrabutylammonium chloride, tetrapentylammonium chloride, tetrahexylammonium chloride, tetraheptylammonium chloride, tetraoctylammonium chloride, tetrahexadecylammonium chloride, tetraoctadecylammonium chloride, benzyltrimethylammonium chloride, benzyltriethylammonium chloride, benzyltributylammonium chloride, 1-methylpyridinium chloride, 1-hexadecylpyridinium chloride, 1,4-dimethylpyridinium chloride, tetramethyl-2-butylammonium chloride, trimethylcyclopropylammonium chloride, tetramethylammonium bromide, tetraethylammonium bromide, tetrapropylammonium bromide, tetrabutylammonium bromide, tetrapentylammonium bromide, tetrahexylammonium bromide, tetraheptylammonium bromide, tetraoctylammonium bromide, tetrahexadecylammonium bromide, tetraoctadecylammonium bromide, benzyltrimethylammonium bromide, benzyltributylammonium bromide, 1-methylpyridinium bromide, 1-hexadecylpyridinium bromide, 1, 4-dimethylpyridinium bromide, trimethyl-2-butylammonium bromide, trimethylcyclopropylammonium bromide, benzyltriethylammonium bromide, tetramethylammonium iodide, tetrabutylammonium iodide, tetraoctylammonium iodide, t-butylethyldimethylammonium iodide, tetradecyltrimethylammonium iodide, hexadecyltrimethylammonium iodide, octadecyltrimethylammonium iodide, benzyltrimethylammonium iodide, benzyltriethylammonium iodide, benzyltributylammonium iodide and the like.

Examples of the quaternary phosphonium salt include tributylmethylphosphonium chloride, triethylmethylphosphonium chloride, methyltriphenoxyphosphonium chloride, butyltriphenylphosphonium chloride, tetrabutylphosphonium chloride, benzyltriphenylphosphonium chloride, hexadecyltrimethylphosphonium chloride, hexadecyltributylphosphonium chloride, hexadecyldimethylethylphosphonium chloride, tetraphenylphosphonium chloride, tributylmethylphosphonium bromide, triethylmethylphosphonium bromide, methyltriphenoxyphosphonium bromide, butyltriphenylphosphonium bromide, tetrabutylphosphonium bromide, benzyltriphenylphosphonium bromide, hexadecyltrimethylphosphonium bromide, hexadecyltributylphosphonium bromide, hexadecyldimethylethylphosphonium bromide, tetraphenylphosphonium bromide, tributylmethylphosphonium iodide, triethylmethylphosphonium iodide, methyltriphenoxyphosphonium iodide, butyltriphenylphosphonium iodide, tetrabutylphosphonium iodide, benzyltriphenylphosphonium iodide, hexadecyltrimethylphosphonium iodide.

Examples of the sulfonium salt include: dibutylmethylsulfonium chloride, trimethylsulfonium chloride, triethylsulfonium chloride, dibutylmethylsulfonium bromide, trimethylsulfonium bromide, triethylsulfonium bromide, dibutylmethylsulfonium iodide, trimethylsulfonium iodide, and triethylsulfonium iodide.

An amount of the phase-transfer catalyst used is usually within the range of about 0.01–0.2 mol, preferably about 0.02–0.1 mol per mol of Compound of the formula [IV].

In this reaction, an organic solvent is usually used. Examples of the solvent include:

a hydrocarbon solvent such as n-n-hexane, cyclonhexane, n-pentane, toluene and xylene;

an ether solvents such as diethyl ether, tetrahydrofuran, dimethoxyethane and anisole;

a halogenated solvent such as chloroform, dichloromethane, 1,2-dichloroethane, monochlorobenzene and o-dichlorobenzene; and an aprotic polar solvent such as N,N-dimethyl formamide, dimethyl sulfoxide, N,N-dimethyl acetamide, hexamethylphosphoric triamide.

The reaction is usually carried out at temperature of from −78° C. to aboiling point of the solvent used, and preferably ranges from 0° C. to 30° C.

The compound of the formula [IV] used above can be produced, for example, by deprotection according to a conventional method as described above in a procedure following step (b) of the compound of the formula [V] having two protected hydroxyl groups.

Process C

The compound of formula [V] can be obtained by a process which comprises reacting a sulfone compound of the formula [VI] with a halohydrin compound of the formula [VII] in the presence of a base.

In the halohydrin compound [VII], X indicates a halogen atom such as a chlorine atom, a bromine atom, an iodine atom or the like.

$R_{10}$ indicates the same protective group as defined for R' above.

The compound of formula [VI] can be produced by a process as disclosed in Chemistry Letters, 1985, 479.

Examples of the base include alkyl lithium, a Grignard reagent, alkali metal hydroxide, alkaline earth metal hydroxide, alkali metal hydride, alkaline earth metal hydride, alkali metal alkoxide and alkaline earth metal alkoxide.

Specific examples thereof include, n-butyllithium, s-butyllithium, t-butyllithium, ethylmagnesium bromide, ethylmagnisium chloride, sodium hydroxide, potassium hydroxide, sodiumhydride, potassium hydride, sodiummethoxide, potassium methoxide, potassium t-butoxide, sodium t-butoxide and the like.

An amount of the base is usually within the range of about 0.1–2 moles per mol of the sulfone compound of the formula [VI].

The phase-transfer catalyst as described above can be used in this reaction. An amount of the phase-transfer catalyst is usually within the range of about 0.01–0.2 mol, preferably about 0.02–0.1 mol per mol of the sulfone compound of the formula [VI].

In this reaction, an organic solvent is usually used. Examples of the solvent include an ether solvent such as diethyl ether, tetrahydrofuran, dimethoxyethane and anisole; a hydrocarbon solvent such as n-hexane, cyclohexane, n-pentane, toluene and xylene; and an aprotic polar solvent such as N,N-dimethyl formamide, dimethyl sulfoxide, N,N-dimethyl acetamide, hexamethylphosphoric triamide.

The reaction is usually carried out at temperature of from −78° C. to a boiling point of the solvent used.

After completion of the reaction, the sulfone compound [V] can be obtained by a usual post-treatment and may be further purified by silica gel chromatography or the like, if necessary.

Process D

The halohydrin compound of the formula [VII'] used above can be produced by a process which comprises reacting a compound of the formula: $R_{12}OH$ wherein $R_{12}$ is an acyl group, with at least one compound selected from halohydrin compounds of the formulae of [VII'a] and [VII'b] in the presence of a strong acid catalyst.

In the halohydrin of the formula of [VII'a] or [VII'b] used in the this process, examples of the acyl group for $R_{11}$ include formyl, acetyl, ethoxyacetyl, fluoroacetyl, difluoroacetyl, trifluoroacetyl, chloroacetyl, dichloroacetyl, trichloroacetyl, bromoacetyl, dibromoacetyl, tribromoacetyl, cyanoacetyl, propionyl, 2-chloropropionyl, 3-chloropropionyl, butyryl, 2-chlorobutyryl, 3-chlorobutyryl, 4-chlorobutyryl, 2-methylbutyryl, 2-ethylbutyryl, valeryl, 2-methylvaleryl, 4-methylvaleryl, hexanoyl, isobutyryl, isovaleryl, pivaloyl, benzoyl, o-chlorobenzoyl, m-chlorobenzoyl, p-chlorobenzoyl, o-acetoxybenzoyl, o-methoxybenzoyl, m-methoxybenzoyl and p-methoxybenzoyl. The acyl group for $R_{11}$ may also include those listed for $R_{12}$ below.

In the halohydrin compound of the formula of [VII'a] or [VII'b], R' indicates a protective group for a hydroxyl group.

Examples of the halogen atom for X include a chlorine atom, a bromine atom and an iodine atom.

Examples of the carboxylic acid of the formula $R_{12}OH$ include an aliphatic carboxylic acid having 1–6 carbon atoms and an aromatic carboxylic acid both of which may be substituted with a halogen atom(s), a (C1–C3)alkoxy group (s), a cyano group(s) or a (C1–C3)acyloxy group.

Specific examples of the aliphatic carboxylic acid include: formic acid, acetic acid, ethoxyacetic acid, fluoroacetic acid, difluoroacetic acid, trifluoroacetic acid, chloroacetic acid, dichloroacetic acid, trichloroacetic acid, bromoacetic acid, dibromoacetic acid, tribromoacetic acid, cyanoacetic acid, propionic acid, 2-chloropropionic acid, 3-chloropropionic acid, n-butyric acid, 2-chloro-n-butyric acid, 3-chloro-n-butyric acid, 4-chloro-n-butyric acid, 2-methyl-n-butyric acid, 2-ethyl-n-butyric acid, n-valeric acid, 2-methyl-n-valeric acid, 4-methyl-n-valeric acid, hexanoic acid, isobutyric acid, isovaleric acid, pivalic acid.

Examples of the aromatic carboxylic acid include: benzoic acid, o-chlorobenzoic acid, m-chlorobenzoic acid, p-chlorobenzoic acid, acetylsalicylic acid, o-anisic acid, m-anisic acid and p-anisic acid. An amount thereof is not particularly limited.

As the strong acid catalyst, an organic acid such as p-toluenesulfonic acid, benzenesulfonic acid, methanesulfonic acid, trifluoromethanesulfonic acid, camphorsulfonic acid and trifluoroacetic acid; strong acid cation-exchange resins such as Nafion (trade mark), Amberlyst (trade mark) and Duolite (trade mark); inorganic acids such as sulfuric acid, hydrochloric acid and perchloric acid are used.

An amount of the strong acid catalyst is usually within the range of about 0.01–0.5 mol, preferably about 0.05–0.3 mol per mol of the halohydrin compound of the formula [VII'a] or [VII'b].

The reaction is usually carried out at temperature of from −78° C. to a boiling point of the solvent used, preferably about 10–30° C.

After completion of the reaction, for example, water is added to the reaction mixture and the mixture is subjected to extraction, phase separation, and concentration of the organic layer to obtain the halohydrin compound of the formula [VII'], which may be further purified by silica gel chromatography, if necessary.

Process E

At least one compound selected from the halohydrin compound of the formula of [VII'a] and [VII'b] can be produced by allowing a triene compound of the formula [VIII] to react with a compound of $R_{11}OH$ wherein $R_{11}$ is a hydrogen atom or an acyl group, and a halogenating agent.

Examples of the halogenating agent include a chlorinating agent such as chlorine, hypochlorous acid, t-butyl hypochlorite, ethyl hypochlorite, sodium hypochlorite, potassium hypochlorite, calcium hypochlorite, N-chlorourea, N-chlorosuccinimide, chloramine-T and chloramine-B; brominating agents such as a bromine, hypobromous acid, calcium hypobromite, N-bromoacetamide and N-bromosuccinimide; and iodinating agents such as an iodine and N-iodosuccinimide.

An amount of the halogenating agent is not particularly restricted, but about one mol of halogenating agent per mol of the triene compound of the formula [VII] is usually used.

As a reaction solvent, an ether such as tetrahydrofuran, dioxane, dimethoxyethane and diethyl ether; an alcohol such as t-butyl alcohol, t-amyl alcohol and 2-propanol; a halogenated hydrocarbon such as dichloromethane, chloroform and carbon tetrachloride; a ketone such as acetone, methyl isopropyl ketone and methyl isobutyl ketone, an aprotic polar solvent such as dimethyl sulfoxide, acetonitrile, N,N-dimethyl formamide and N,N-dimethyl acetamide. An amount of the solvent is not particularly limited.

When $R_{11}$ indicates an acyl group, the acyl group include those described for $R_{12}$ above.

An amount of the carboxylic acid is not particularly limited, but it is usually within the range from about 1 mol to about 10 moles per mol of the triene compound [VIII].

The reaction is usually carried out within a temperature range from about 15 to 120° C.

In this process water can be used in place of the carboxylic acid, $R_{11}$ indicating a hydrogen atom. An amount of water is usually in the range of about 1–100 moles, preferably in the range of about 1–10 moles per mol of the triene compound of the formula [VII]. The reaction is usually carried out at temperature of from −78° C. to a boiling point of the solvent used, preferably 0–30° C.

After completion of the reaction, the halohydrin compounds [VII'a] and [VII'b] can be obtained by a conventional post-treatment. These regio isomers can be separated and purified by silica gel chromatography.

When the halohydrin compound [VII'] has a protective group other than an acyl group for $R_{10}$, such a halohydrin compound can be obtained by protecting either a hydroxyl group of the halohydrin compounds [VII'b] wherein $R_{11}$ is a hydrogen atom, or that obtained by deprotecting the acyl group $R_{12}$ of the halohydrin compound [VII'].

The deprotection is usually conducted according to a deprotecting process as described above following Process A.

Process F

The triene compound of the formula [VIII] can be produced by a process which comprises reacting a compound of the formula [IX] with a base in the presence of a palladium catalyst.

An alkali metal hydroxide such as sodium hydroxide or potassium hydroxide in a form of fine powder is usually used in this reaction. An amount of the base used is usually about 1–5 moles per mol of the compound of the formula [IX].

Examples of the palladium catalyst include allylpalladium chloride dimer, palladium acetate, palladium oxide, palladium propionate, dichlorobis(triphenylphosphine) palladium, palladium di-$\mu$-chlorobis ($\eta$-allyl), palladium dichloro ($\eta$-1, 5-cyclooctadiene), palladium dichloro ($\eta$-2, 5-norbornadiene), palladium dichlorobis(acetonitrile), palladium dichlorobis(benzonitrile), palladium dichlorobis(N, N-dimethyl formamide), palladium bis(acetylacetonato) and the like. Allylpalladium chloride dimer is particularly preferably used.

An amount of the palladium catalyst is usually 0.05% by weight or more, preferably 1% by weight or more per mol of the compound [IX]. Although the upper limit is not restricted, it is preferably 5% by weight of less for economic reasons.

The reaction is usually carried out in the co-presence of a phase-transfer catalyst in order to accelerate the reaction.

Examples of the phase-transfer catalyst include a quaternary ammonium salt, a quaternary phosphonium salt and a sulfonium salt as described above.

An amount of the phase-transfer catalyst is usually 0.01–0.1 part by weight, preferably 0.02–0.1 part by weight of Compound [IX].

An anhydrous solvent is usually used in this reaction, and examples thereof include an aprotic polar solvent such as N,N-dimethyl formamide, dimethyl sulfoxide and N,N-dimethyl acetamide; an ether such as diethyl ether and tetrahydrofuran; an aromatic hydrocarbon such as toluene and xylene; an ester such as ethyl acetate or methyl formate; a ketone such as acetone; and an alcohol such as methanol, ethanol, i-propyl alcohol or t-butyl alcohol. The reaction is usually carried out at temperature from about 10° C. to a boiling temperature of the solvent used.

After completion of the reaction, the triene compound [VIII] can be obtained by a conventional post-treatment, and may be further purified by silica gel chromatography, if necessary.

A compound of the formula [IX] can by easily synthesized by a known method.

The present invention will be further illustrated by the following Examples, but are not to be construed to limit the scope of the present invention thereto.

EXAMPLE 1

0.5 g (0.995 mmol) of 1-acetoxy-5-hydroxy-3,7-dimethyl-9-(2,6,6-trimethylcyclohexene-1-yl)-9-(4-methylphenylsulfonyl)-nona-2,6-diene (compound III-1) and 10 ml of tetrahydrofuran were added into a dry four-necked flask in an atmosphere of nitrogen. After dissolving compound [III-1], 0.095 g (0.497 mmol) of titanium tetrachloride was added slowly to the solution at room temperature. After stirring at the temperature for twelve hours, disappearance of the starting material was confirmed by TLC. The reaction mixture was added to 1% aqueous solution of sodium hydroxide and was extracted with ether. The organic layer was dried over anhydrous magnesium sulfate and then concentrated to give a crude product. The crude product obtained was purified by silica gel chromatography to give a compound as pale yellow oil.

EXAMPLE 2

0.02 g of the compound obtained in Example 1 and 5 ml of cyclohexane were added into a dry four-necked flask under nitrogen flow. After dissolving the mixture, 0.058 g (0.825 mmol) of potassium methoxide was added to the solution and the mixture was stirred at 40° C. for six hours.

After confirming disappearance of the starting materials by TLC, the reaction mixture was added to a saturated aqueous solution of ammonium chloride and was extracted with ethyl acetate. The organic layer was washed with a saturated aqueous solution of ammonium chloride again and was dried over anhydrous magnesium sulfate. The solvent was removed from the organic layer to give a crude product as pale yellow oil. It was confirmed by NMR that the obtained compound contained, as a main component, retinol having only trans-configurations.

In a dry four-necked flask, 0.01 g (0.035 mmol) of the above crude product was dissolved in 5 ml of toluene in an atmosphere of nitrogen. Then, after adding 0.003 g (0.035 mmol) of pyridine and 0.4 mg (0.004 mmol) of 4-dimethylaminopyridine, 0.004 g (0.035 mmol) of acetic anhydride was slowly added to the mixture at room temperature, and the mixture obtained was stirred at that temperature for four hours. After confirming disappearance of the starting materials by TLC, 5% of an aqueous solution of hydrochloric acid and toluene were added to the mixture. After washing the mixture with that aqueous solution and was separated into two layers. The organic layer obtained was washed with a saturated aqueous solution of sodium hydrogencarbonate and a saturated aqueous solution of sodium chloride, in order, and then dried over anhydrous magnesium sulfate. The dried organic layer was concentrated to give a crude product as yellow oil. The crude product obtained was purified by silica gel column chromatography. It was confirmed, by a comparison of its NMR with that of a standard sample of all trans-retinol acetate, that retinol acetate containing solely trans-configurations as a main component was obtained.

EXAMPLE 3

In a dry flask, 60 mg (0.13 mmol) of 1,5-dihydroxy-3,7-dimethyl-9-(2,6,6-trimehylcyclohexene-1-yl)-9-(4-methylphenysulfonyl)-nona-2,6-diene (hereinafter, referred to as compound [IV-1]) was charged and dissolved in 20 ml of n-hexane, and 3.4 mg (0.013 mmol) of n-dodecyltrimethylammonium chloride, 14 mg (0.13 mmol) of sodium carbonate and 13.3 mg (0.13 mmol) of acetic anhydride were added thereto. After stirring at room temperature for twenty hours, disappearance of the starting material was confirmed, and then water was added to the reaction mass. After extracting with ether, the organic layer was washed with an aqueous solution of ammonium chloride and a saturated aqueous solution of sodium chloride in order. After drying over anhydrous magnesium sulfate, the organic layer was concentrated to give a crude product. The crude product was purified by silica gel chromatography to give 1-acetoxy-5-hydroxy-3,7-dimethyl-9-(2,6,6-trimethylcyclohexene-1-yl)-9-(4-methylphenylsulfonyl)-nona-2,6-diene (hereinafter, referred to as compound [III-1]) in a yield of 92%.

Compound [III-1] $^1$H-NMR δ (CDCl$_3$) 0.82(6H,s), 1.00 (6H,s), 1.42(3H,s), 1.73(3H,s), 2.01(3H,s), 2.05(3H,s), 2.45 (3H,s), 2.58–3.01(2H,m), 3.89(1H,t,J=7 Hz), 4.29–4.37(1H, m), 4.58(1H,d,J=7 Hz), 5.14(1H,d,J=8 Hz), 5.23(1H,d,J=8 Hz), 5.41(1H,t,J=7 Hz), 7.31(2H,d,J=8 Hz), 7.75(2H,d,J=8 Hz)

EXAMPLE 4

0.53 g (1.8 mmol) of β-cyclogeranil p-tolylsulfone (hereinafter, referred to as compound [VI-1]) was added and dissolved in 20 ml of tetrahydrofuran, and then the solution obtained was cooled to -60° C. At the temperature, 1.13 ml of n-hexane solution containing 1.18 mmol of n-butyllithium was dropped to that solution and the mixture obtained was maintained at that temperature. Then, 5 ml of tetrahydrofuran solution of 0.3 g (0.9 mmol) of 8-bromo-3, 7-dimethyl-octa-2,6-diene-1,5-diacetate (hereinafter, referred to as compound [VII-1]) was dropped in one hour. After stirring the mixture at that temperature for three hours, disappearance of the starting material was confirmed by TLC. The reaction mass was discharged into a saturated aqueous ammonium chloride solution and extracted with ether. The organic layer obtained was washed with a saturated aqueous solution of sodium chloride and dried over anhydrous magnesium sulfate. After removing the solvent, a crude product was obtained. The crude product obtained was purified by silica gel column chromatography to isolate 1,5-diacetoxy-3,7-dimethyl-9-(2,6,6-trimethylcyclohexene-1-yl)-9-(4-methylphenylsulfonyl)-nona-2,6-diene (hereinafter, referred to as Compound [V-1]) as pale yellow oil in a yield of 74%. (Rf value: 0.38; n-hexane:ethyl acetate 3:1).

Compound [V-1]

$^1$H-NMR δ (CDCl$_3$) 0.76(6H,d,J=14 Hz), 0.95(6H,d,J=14 Hz), 1.39(3H,s), 1.70(3H,s), 2.01(3H,s), 2.03(3H,s), 2.44 (3H,s), 2.66–2.95(2H,m), 3.82-3.86(1H,m), 4.53(2H,d,J=7 Hz), 5.10(1H,d,J=9 Hz), 5.20(1H,d,J=9 Hz), 5.34(1H,br), 5.56(1H,br), 7.33(2H,d,J=8 Hz), 7.76(2H,d,J=8 Hz).

$^{13}$C-NMR δ (CDCl$_3$) 15.1,16.0,16,1,16.6,18.8,20.8,20.9, 21.4,28.2,29.0,35.5,40. 5,40.8,44.6,60.8,65.3.65.5,65.7, 68.3,68.5,68.8,121.9,127.1 ,128.3,129.4,130.5,130.6,136.2, 137.1,137.6,137.7,138.4,144 .0,169.8,170.0,170.7.

EXAMPLE 5

To 0.53 g (1.8 mmol) of compound [VI-1], 16 ml of tetrahydrofuran and 4 ml of hexamethylphosphoric triamide were added, and the compound [VI-1] was dissolved in the solvents. Then, 0.072 g (1.8 mmol) of sodium hydroxide and 0.058 g (0.18 mmol) of tetra-n-butylammonium bromide were added to the solution at room temperature and the mixture was maintained at 40–45° C. for three hours. After cooling the mixture to -60° C., 5 ml of tetrahydrofuran solution of 0.3 g (0.9 mmol) of compound [VII-1] was dropped in one hour. After stirring at that temperature for five hours, the mixture was heated to 60° C. and stirred at that temperature for five hours. After confirming by TLC of disappearance of one starting compound, the reaction mass was discharged to a saturated aqueous solution of ammonium chloride and extracted with ether. The organic layer obtained was washed with a saturated aqueous solution of sodium chloride and dried over anhydrous magnesium sulfate. After removing the solvent, a crude product was obtained. The crude product obtained was purified by silica gel column chromatography to isolate compound [V-1] as pale yellow oil in a yield of 51%.

EXAMPLE 6

To 0.53 g (1.8 mmol) of compound [VI-1], 20 ml of N,N-dimethyl acetamide were added, and the compound [VI-1] was dissolved in the solvent. Then, 0.072 g (1.8 mmol) of sodium hydroxide and 0.058 g (0.18 mmol) of tetra-n-butylammonium bromide were added to the solution at 0° C., and 5 ml of tetrahydrofuran solution of 0.3 g (0.9 mmol) of compound [VII-1] was dropped at 0° C. in one hour. After stirring the mixture at that temperature for thirty minutes, the mixture was heated to 50° C. and stirred at that temperature for five hours. After confirming by TLC of disappearance of one starting compound, the reaction mass was discharged to a saturated aqueous solution of ammonium chloride and extracted with ether. The organic layer obtained was washed with a saturated aqueous solution of sodium chloride and dried over anhydrous magnesium sulfate. After removing the solvent, a crude product was obtained. The crude product obtained was purified by silica gel column chromatography to isolate the compound [V-1] as pale yellow oil in a yield of 59%.

EXAMPLE 7

0.10(0.18 mmol) g of compound [V-1], 20 ml of t-butyl alcohol and 20 ml of water were added into a dry flask, and 0.20 g (1.80 mmol) of potassium t-butoxide was added to the mixture under stirring. After stirring at 40° C. for four hours, disappearance of the starting compound was confirmed by TLC, and then a saturated aqueous solution of ammonium chloride was added to the reaction solution, followed by extracting with ether. Organic layers obtained were combined and washed with an aqueous solution of sodium chloride. The combined organic layer was dried over anhydrous magnesium sulfate and concentrated to give a mixture including three components. The mixture obtained was separated by silica gel column chromatography to give 1-acetoxy-5-hydroxy-3,7-dimethyl-9-(2,6,6-trimethylcyclohexene-1-yl)-9-(4-methylphenylsulfonyl)-nona-2, 6-diene [III-1] in a yield of 31% and 5-acetoxy-1-hydroxy-3,7-dimethyl-9-(2,6,6-trimehylcyclohexene- 1-yl)-9-(4-methylphenylsulfonyl)-nona-2,6-diene [V-2] in a yield of 37%.

Compound [III-1] $^1$H-NMR δ (CDCl$_3$) 0.82(6H,s),1.00 (6H,s),1.42(3H,s),1.73(3H,s),2.01(3H,s),2.0 5(3H,s),2.45 (3H,s),2.58–3.01(2H,m),3.89(1H,t,J=7 Hz),4.29-4.37(1H, m),4.58(1H,d,J=7 Hz),5.14(1H,d,J=8 Hz),5.23(1H,d,J=8 Hz),5.41(1H,t,J=7 Hz),7.31(2H,d,J=8 Hz),7.75(2H,d,J=8 Hz)

Compound [V-2] $^1$H-NMR δ (CDCl$_3$) 0.70(6H,d,J=26 Hz),0.88(6H,d,J=26 Hz),1.93(3H,s),1.97(3H,s), 2.37(3H,s), 2.52–2.90(2H,m),3.77-3.84(1H,m),4.03(2H,t,J=7 Hz), 5.05–5.14(1H, m),5.33-5.36(1H,lm),5.49, 5.51(1H,m),7.24 (2H,d,J=8 Hz), 7.68(2H,d,J=8 Hz)

EXAMPLE 8

100 mg(0.34 mmol) of 8-bromo-7-hydroxy-3,7-dimethyl-2,5-octadienyl acetate was added, under stirring at 25° C., to a mixed solution of 0.4 ml of acetic anhydride and 1 ml of acetic acid containing 20 mg (0.10 mmol) of p-toluenesulfonic acid. After stirring the mixture at 25° C. for 25 minutes, 4 ml of ion-exchange water, and the mixture obtained was extracted with 1 ml of n-hexane. The organic layer was washed with a 5% aqueous solution of sodium hydrogencarbonate, followed by drying with anhydrous sodium sulfate. The organic layer obtained was concentrated under reduced pressure to give 58 mg of pale yellow oil containing 88% of 5-acetoxy-8-bromo-3,7-dimethyl-2,6-octadienyl acetate [VIII-1]. The pure yield was 51%.

EXAMPLE 9

260 mg (2.6 mmol) of sulfuric acid was added, under stirring at 0° C., to a mixed solution of 40 ml of acetic acid and 40 ml of tetrahydrofuran containing 17.36 g (52.1 mmol) of a 1:1 mixture of 5-acetoxy-8-bromo-3,7-dimethyl-2,6-octadienyl acetate [VII'b-1] and 7-acetoxy-8-bromo-7-hydroxy-3,7-dimethyl-2,5-octadienyl acetate [VII'a-1]. After stirring the mixture at 0° C. for four hours and at 25° C. for twenty hours, 120 ml of ion-exchange water and 120 ml of n-hexane were added to the mixture. After separating the mixture in layers, the water layer was further extracted with 80 ml of n-hexane in 40 ml portions. The combined organic layer was washed with 40 ml of a 5% aqueous solution of sodium hydrogencarbonate and 40 ml of a saturated aqueous solution of sodium chloride in order, and then dried over anhydrous sodium sulfate. After concentrating the organic layer under reduced pressure, 16.47 g of reddish brown oil, which contained 77% of 1,4-adduct produced in a yield of 73%, was subjected to silica gel chromatography using an eluent consisting of n-hexane and ethyl acetate in a ratio of n-hexane to ethyl acetate being 10:1 to give 6.91 g of 1,4-adduct(5-acetoxy-8-bromo-3,7-dimethyl-2, 6-octadienyl acetate [VII'-1], as pale yellow oil, in a yield of 40%.

Compound [VII'-1]

Rf: 0.49 (adsorbent: silica gel, eluent; n-hexane:ethyl acetate=3:1)

$^1$H-NMR δ (CDCl$_3$) 1.74(3H,s),1,85(3H,s),2.02(3H,s), 2.05(3H,s),2.23(1H,dd,J=13.5 Hz, 5.9 Hz),2,38(1H,dd,J= 13.5 Hz,7.3 Hz),3.91(2H,s),4.56(2H, d,J=6.9 Hz),5.38(1H, t,J=6.9 Hz),5.51(1H,d,J=9.2 Hz),5.59(1H,d dd,J=9.2 Hz,7.3 Hz,5.9 Hz)

EXAMPLE 10

A mixed solution of 40 ml of dimethyl sulfoxide containing 5.16 g (26.6 mmol) of 3,7-dimethyl-2,5,7-octatrienyl acetate[VIII-l] and 0.48 g (26.6 mmol) of ion-exchange water was cooled to 10° C., and 4.78 g (26.6mmol) of N-bromosuccinimide was added to the mixture. The mixture was stirred at room temperature for forty minutes. After confirming disappearance of the starting compound by gas chromatography, 40 ml of ion-exchange water was added. Then 40 ml of ethyl acetate was further added and an organic layer was separated. The water layer was extracted with 70 ml of ethyl acetate in 35 ml portions. The combined organic layer was washed with 20 ml of 5% aqueous solution of sodium hydrogencarbonate and 20 ml of a saturated aqueous solution of sodium chloride in order and then dried over anhydrous sodium sulfate. 9.12 g of yellow oil which was obtained by concentrating the organic layer under reduced pressure was subjected to silica gel column chromatography using an eluent consisting of n-hexane and ethyl acetate in a ratio of n-hexane to ethyl acetate being 5:1 and subsequently 3:1 to give 4.84 g of 8-bromo-7-hydroxy-3,7-dimethyl-2,5-octadienyl acetate[VII'a-2] in a yield of 63% and 1.28 g of 8-bromo-5-hydroxy-3,7-dimethyl-2,6-octadienyl acetate [VII'b-2] in a yield of 17%.

Compound [VII'a-2]

Rf: 0.30 (adsorbent: silica gel, eluent; n-hexane:ethyl acetate=3:1)

$^1$H-NMR δ (CDCl$_3$): 1.43(3H,s),1.70(3H,s),2.06(3H,s), 2.34(1H,s),2.78(2H,d,J=6. 9 Hz),3.47(2H,s),4.59(2H,d,J= 6.6 Hz),5.38(1H,t,J=6.6 Hz),5.57 (1H,d,J=15.5 Hz),5.74 (1H,dt,J=15.5 Hz,6.9 Hz)

$^{13}$C-NMR δ (CDCl$_3$) 16.43,20.94,26.15,41.98,45.00, 61.17,71.27,119.43,127.67,13 5.38,140.29,170.98

Compound [VII'b-2]

Rf: 0.14 (adsorbent: silica gel, eluent; n-hexane:ethyl acetate=3:1)

$^1$H-NMR δ (CDCl$_3$) 1.76(s,3H), 1.82(s,3H),2.06(s,3H), 2.20(dd,J=13.5 Hz,5.6 Hz,1H), 2.30(dd,J=13.5 Hz,7.9 Hz,1H), 2.67(brS,1H),3.95(s,2H), 4.49(ddd,J=8.6 Hz,7.9 Hz,5.6 Hz, 1H), 4.59(d,J=6.9 Hz,2H), 5.42(t,J=6.9 Hz,1H), 5.58(d,J=8.6 Hz,1H)

$^{13}$C-NMR δ (CDCl$_3$) 14.94,16.62,20.76,40.07,46.81, 60.90,66.09,121.92,132.65,13 3.72,137.48,170.89

EXAMPLE 11

20.11 g (0.1 mol) of 3,7-dimethyl-2,5,7-octatrienyl acetate [VIII-1] and 100 ml of acetic acid were added in a flask, and then 18.3 g (0.1 mol) of N-bromosuccinimide was added to the mixture slowly. After stirring of 10–15 minutes at room temperature, the reaction mass became homogeneous. After two hours, disappearance of the starting compounds was confirmed by TLC, the reaction mixture was discharged into water, followed by being extracted with toluene. The organic layer was dried over anhydrous magnesium sulfate, and then was concentrated to give an about 1:1 mixture of compound [VII'b-1] and [VII'a-1] in a yield of 95%. The mixture obtained was separated and purified by silica gel chromatography, as a result, 8-bromo-3,7-dimethyl-octa-2,6-diene-1,5-diacetate [VII'b-1] was isolated as pale yellow oil in a yield of 29%, Compound[VII'a-1] in a yield of 30% and in a yield of 31% as a mixture.

Compound [VII'b-1] $^1$H-NMR δ (CDCl$_3$) 1.77(3H,s), 1.82(3H,s), 1.98(3H,s), 2.02(3H,s), 2.29(2H,ddd, J=35 Hz, 8 Hz, 6 Hz), 3.89(2H,s), 4.55(2H,d,J=7 Hz), 5.37(1H,t,J=7 Hz), 5.48~5.62(2H,m)

Compound [VII'a-1] $^1$H-NMR δ (CDCl$_3$) 1.65(3H,s), 1.68(3H,s), 2.05(3H,s), 2.06(3H,s), 2.78(2H,d,J=6 Hz), 3.75 (2H,dd, J=26 Hz,11 Hz), 4.57(2H,d, J=7 Hz), 5.35(1H,t,J=7 Hz), 5.61~5.77(2H,m).

EXAMPLE 12

Into a dry four-necked flask, 6.8 g (0.17 mol) of finely powdered sodium hydroxide, 2.2 g (8.5 mmol) of triphenylphosphine, 1.4 g (5.1 mmol) of tetra-n-butylammonium chloride, 0.62 g (1.7 mmol) of allylpalladium chloride dimer and 100 ml of tetrahydrofuran were added. 150 ml of a tetrahydrofuran solution of 40 g (0.17 mol) of 6-chloro-3, 7-dimethyl-octa-2,7-dienyl acetate[IX-1] was dropped to the mixture with stirring at room temperature in one hour. After stirring at room temperature for three days, disappearance of the starting compounds was confirmed by TLC and the reaction was completed. The reaction mixture was discharged into water and extracted with ether. The organic layer was washed with a saturated aqueous solution of sodium chloride and dried over anhydrous magnesium sulfate. The organic layer dried was concentrated to give a crude product. The crude product was purified by silica gel chromatography to give 3,7-dimethyl-2,5,7-octatrienyl acetate[VIII-1] as pale yellow oil in a yield of 65%.

Compound[VIII-1] $^1$H-NMR δ (CDCl$_3$) 1.70(3H,s), 1.85 (3H,s), 2.08(3H,s), 2.81(2H,d,J=7 Hz), 4.58(2H,d,J=7 Hz), 4.90(2H, s), 5.37(1H,t,J=7 Hz), 5.61(1H,td, J=16 Hz,7 Hz), 6.16(1H,d,J=15 Hz)

Comparative Example 1

When the reaction and post-treatment were conducted in the same manner as that described in Example 12 without using 2.2 g (8.5 mmol) of triphenylphosphine, 1.4 g (5.1 mmol) of tetra-n-butylammonium chloride and 0.62 g (1.7 mmol) of allyl palladium chloride dimer, the aimed product was not obtained, but unreacted 6-chloro-3,7-dimethyl-2,7-octadiene [IX-1] was recovered as pale yellow oil. The recovering yield was 90%.

REFERENTIAL EXAMPLE 1

40 g (20.4 mmol) of geranil acetate was dissolved in 100 ml of n-hexane. After adding 17.1 g (70.0 mmol) of trichloroisocyanuric acid slowly, the mixture was maintained at −10° C. to 0° C. for six hours. After the completion of the reaction, remaining trichloroisocyanuric acid and by-produced isocyanuric acid were removed out of the system by filtration. The filtrate was washed with a 5% aqueous solution of sodium hydrogencarbonate and ion-exchange water in order, and dried over anhydrous sodium sulfate. After removal of the solvent, a crude product was obtained. The crude product was subjected to silica gel column chromatography to give desired 6-chloro-3,7-dimethyl-2,7-octatrienyl acetate as pale yellow oil in a yield of 86%.

What is claimed is:

1. A compound of the formula (I):

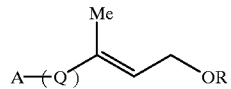

wherein R represents a hydrogen atom or a protective group for a hydroxyl group; and A represents a hydrogen atom, a halogen atom or a group of the formula A1:

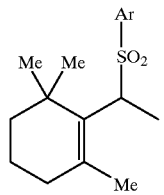

wherein Ar represents an aryl group which may be substituted; and when A represents A1, Q represents Q3:

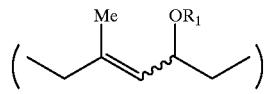

wherein $R_1$ represents a hydrogen atom or a protective group for a hydroxyl group; and when A represents a halogen atom, Q represents Q3 as defined above or Q4:

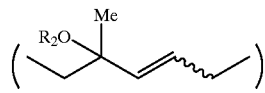

wherein $R_2$ represents a hydrogen atom or a protective group for a hydroxyl group; and when A represents a hydrogen atom, Q is Q2:

, and

R represents
an aliphatic acyl group having 1–6 carbon atoms or an aromatic acyl group both of which may be substituted with a halogen atom, a (C1–C3)alkoxy group, a cyano group or a (C1–C3) acyloxy group,
a silyl group which is substituted with three groups selected from a group consisting of a phenyl group and a (C1–C6) lower alkyl group,
a tetrahydrofuranyl, tetrahydropyranyl, methoxymethyl, methoxyethoxymethyl, 1-ethoxyethyl, allyoxycarbonyl or 2,2,2-trichloroethoxycarbonyl group.

2. A compound according to claim 1, wherein A is A1 and Q is Q3.

3. A compound according to claim 1, wherein A is a halogen atom.

4. A compound according to claim 3, wherein Q is Q3.

5. A compound according to claim 4, wherein $R_1$ is an acyl group.

6. A compound according to claim 3, wherein Q is Q4.

7. A compound according to claim 6, wherein $R_2$ is an acyl group.

8. A process for producing retinol of the formula (X):

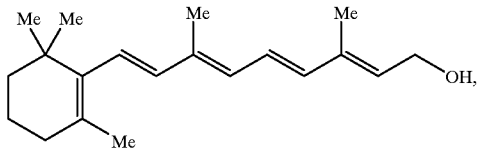

which comprises the steps of:
(a) subjecting a compound of the formula (III)

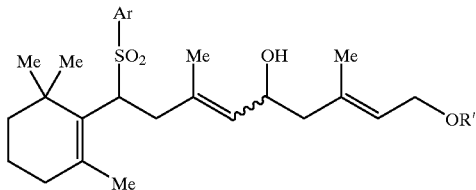

wherein Ar represents an aryl group which may be substituted, and R' represents a protective group for a hydroxyl group, to a reaction in the presence of titanium tetrachloride, and (b) reacting the resulting compound in step (a) with a base.

9. A process for producing a compound of the formula (III):

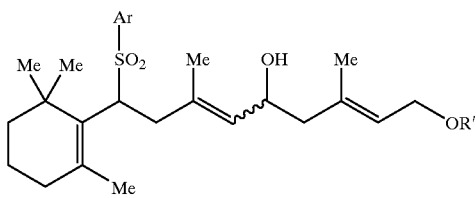

wherein Ar is an aryl group which may be substituted and R' is a protective group for a hydroxyl group, which comprises reacting a compound of the formula (IV):

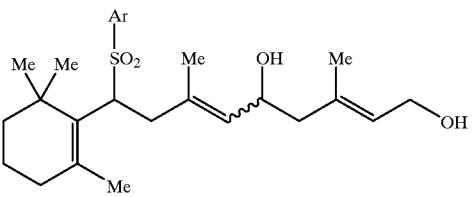

wherein Ar is the same as defined above, with a protective agent selected from acyl halide or acid anhydride in the presence of a base and a phase transfer catalyst.

10. A process according to claim 9, wherein said protective agent is acetyl halide or acetic anhydride.

11. A process according to claim 9, wherein said phase transfer catalyst is a quaternary ammonium salt.

12. A process according to claim 9, wherein the amount of said phase transfer catalyst is 0.01 to 0.2 mol per mol of the compound of the formula (IV).

13. A process according to claim 9, wherein the base is an inorganic base.

14. A process according to claim 9, wherein the inorganic base is selected from an alkali metal, an alkaline earth metal hydroxide, a carbonate salt of an alkali metal, an alkaline earth metal, a hydrogencarbonate of an alkali metal and an alkaline earth metal.

15. A process for producing a compound of the formula (V):

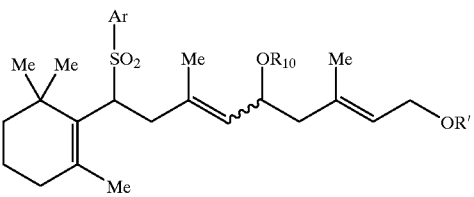

wherein Ar represents an aryl group which may be substituted, $R_{10}$ and R' are the same or different and represent a protective group for a hydroxyl group, which comprises reacting a sulfone compound of the formula (VI):

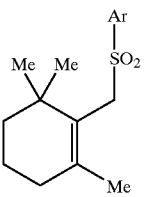

wherein Ar is the same as defined above, with a halohydrin compound of the formula (VII):

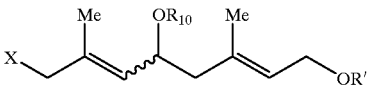

wherein $R_{10}$ and R' are as defined above, and X represents a halogen atom, in the presence of a base.

16. A process according to claim 15, wherein the base is selected from an alkyl lithium, an alkali hydroxide, an alkaline earth metal hydroxide, an alkali metal hydride, an alkaline earth metal hydride, an alkali metal alkoxide, an alkaline earth metal alkoxide and a Grignard reagent.

17. A process according to claim 15, wherein said reaction is conducted in the co-presence of a phase transfer catalyst.

18. A process according to claim 17, wherein said phase transfer catalyst is a quaternary ammonium salt.

19. A process according to claim 18, wherein said quaternary ammonium salt is a quaternary ammonium salt having a group optionally selected from the group consisting of an (C1–C24) alkyl group and an aryl group.

20. A process for producing a halohydrin compound of the formula (VII'):

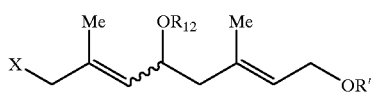

wherein $R_{12}$ represents an acyl group and R' represents a protective group for a hydroxyl group, and X represents a halogen atom, which comprises reacting at least one halohydrin compound selected from the group consisting of a compound of the formula (VII'a):

and a compound of the formula (VII' b):

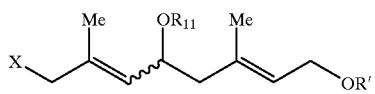

wherein $R_{11}$ represents an acyl group or a hydrogen atom and R' represents a protective group for a hydroxyl group, with a carboxylic acid of the formula:

$R_{12}OH$ wherein $R_{12}$ is the same as defined above, in the presence of a strong acid catalyst.

21. A process according to claim 20, wherein the strong acid catalyst is a sulfonic acid.

22. A process according to claim 21, wherein the sulfonic acid is selected from sulfuric acid, p-toluenesulfonic acid, benzenesulfonic acid, methanesulfonic acid, trifluoromethanesulfonic acid, camphorsulfonic acid, NAFION, AMBERLYST and DUOLITE.

23. A process according to claim 22, wherein $R_{12}$ is an acetyl group.

24. A process for producing at least one halohydrin compound selected from the group consisting of the formula (VII'a):

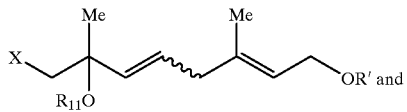

a compound of the formula (VII'b):

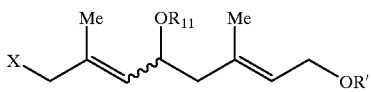

wherein $R_1$ represents an acyl group or a hydrogen atom and R' represents a protective group for a hydroxyl group, which comprises reacting a triene compound of the formula (VIII):

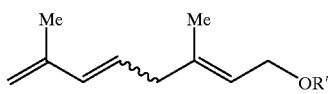

wherein R' is the same as defined above, with a halogenating agent and a compound of the formula:

$R_{11}OH$ wherein $R_{11}$ is the same as defined above.

25. A process for producing the triene compound of the formula (VIII) as defined in claim 24, which comprises reacting a compound of the formula (IX):

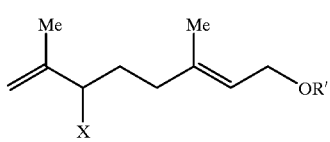

wherein X is a halogen atom and R' is a protective group for a hydroxyl group, with a base in the presence of a palladium catalyst, a phosphine ligand and a phase transfer catalyst.

26. A process according to claim 24, wherein said triene compound of the formula (VIII) is a triene compound obtained by the process of reacting a compound of the formula (IX):

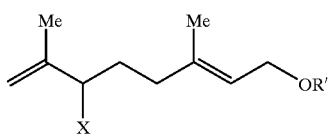

wherein X is a halogen atom and R' is a protective group for a hydroxyl group, with a base in the presence of a palladium catalyst, a phosphine ligand and a phase transfer catalyst.

27. A process according to claim 25, wherein said base is an alkali hydroxide, an alkaline earth metal hydroxide, an alkali metal hydride, an alkaline earth metal hydride, an alkali metal alkoxide or an alkaline earth metal alkoxide.

28. A compound according to claim 1, wherein R is an acyl group.

29. A process according to claim 9, wherein 0.1 to 1.1 moles of the protective agent is used per mol of a compound of the formula (IV).

30. A process according to claim 9, wherein the protective agent is reacted with a compound of the formula (IV) at a temperature ranging from 0° C. to 30° C.

31. A compound according to claim 1, wherein

A represents a hydrogen atom, Q is Q2:

, and

R represents an aliphatic acyl group having 1–6 carbon atoms or an aromatic acyl group, both of which may be substituted with a halogen atom, a (C1–C3)alkoxy group, a cyano group, or a (C1–C3) acyloxy group, a tetrahydrofuranyl, tetrahydropyranyl, methoxymethyl, methoxyethoxymethyl, 1-ethoxyethyl group, or a silyl group which is substituted with three groups selected from the group consisting of a phenyl group and a (C1–C6)lower alkyl group.

32. A compound according to claim 31, wherein

R represents an acetyl, pivaloyl, trimethylsilyl, t-butyldimethylsilyl, t-butyldiphenylsilyl, tetrahydrofuranyl, tetrahydropyranyl, methoxymethyl, methoxyethoxymethyl or 1-ethoxyethyl group.

33. A compound according to claim 31, wherein

R represents an acetyl group.

* * * * *

UNITED STATES PATENT AND TRADEMARK OFFICE
CERTIFICATE OF CORRECTION

PATENT NO.   : 6,348,622 B1  Page 1 of 1
DATED        : February 19, 2002
INVENTOR(S)  : Toshiya Takahashi, Shinzo Seko and Takashi Miki It is certified that error appears in the above-identified patent and that said Letters Patent is hereby corrected as shown below:

<u>Title page,</u>
Item [56], References Cited, OTHER PUBLICATIONS, the following references should be added:
-- A. Oehlschlager et al: J. Org. Chem., vol. 48, No. 25, 1983, pp. 5009-5017, XP002133294.
Chemical Abstracts, vol. 98, No. 19, May 9, 1983, XP002133298.
B. Ceskis et al: Izv. Akad. Nauk. SSSR, Ser. Khim., No. 11, 1982, pp. 2548-2551, Abstract -XP002133296.
Chemical Abstracts, vol. 96, No. 21, -May 24, 1982, XP002133299.
Y. Masaki et al: "Tennen Yuki Kagobutsu Toronkai Koen Yoshishu 24th, pp. 269-276" 1981, Abstract -XP002133297.
G. Koehler et al: Z. Chem., vol. 24, No. 9, 1984, pp. 325-326, XP002133295. --;
Below OTHER PUBLICATIONS, "(List continued on next page)" should be deleted.

Signed and Sealed this

Second Day of July, 2002

Attest:

JAMES E. ROGAN
Attesting Officer   Director of the United States Patent and Trademark Office

UNITED STATES PATENT AND TRADEMARK OFFICE
CERTIFICATE OF CORRECTION

PATENT NO.     : 6,348,622 B1                                    Page 1 of 1
DATED          : February 19, 2002
INVENTOR(S)    : Toshiya Takahashi et al.

It is certified that error appears in the above-identified patent and that said Letters Patent is hereby corrected as shown below:

<u>Title page,</u>
Item [56] References Cited, please insert the following:

-- U.S. PATENT DOCUMENTS
        4,543,433    09/1985    Mignani et al.
        4,825,006    04/1989    Otera et al.
        4,876,400    10/1989    Otera et al. --

Item [56], "FOREIGN PATENT DOCUMENTS", please insert the following references:

-- EP    0152324    08/1985
       JP    58-52267A    03/1983 --

Item [56], "OTHER PUBLICATIONS", please insert the following references:

-- Otera et al., Chemistry Letters, pp. 1883-1885 (1985).
       Babler et al., J. Org. Chem., Vol. 44, No. 10, pp. 1716-1717 (1979).
       Fischli et al., Helvetica Chimica Acta, Vol. 59, Fasc. 2, pp. 397-405 (1976).
       Ivanov et al., Synthesis, pp. 732-734 (1979). --

Signed and Sealed this

Twenty-fourth Day of December, 2002

JAMES E. ROGAN
*Director of the United States Patent and Trademark Office*